United States Patent [19]
Ferreira et al.

[11] Patent Number: 5,672,163
[45] Date of Patent: Sep. 30, 1997

[54] OSTOMY POUCH WITH INTERVENING MEMBRANE AND SUPERABSORBENT

[75] Inventors: Adolfo A. Ferreira, Montgomery, N.J.; Gary E. Oberholtzer, Feasterville, Pa.

[73] Assignee: Bristol-Myers Squibb Company, New York, N.Y.

[21] Appl. No.: 639,873

[22] Filed: Apr. 26, 1996

[51] Int. Cl.⁶ ............................................. A61F 5/44
[52] U.S. Cl. ................................. 604/333; 604/342
[58] Field of Search ........................... 604/332–344

[56] References Cited

U.S. PATENT DOCUMENTS 5,306,264  4/1994  Ferguson et al. ................... 604/333

FOREIGN PATENT DOCUMENTS 2094153  9/1982  United Kingdom ................... 604/333

Primary Examiner—Robert A. Clarke
Attorney, Agent, or Firm—Stuart E. Krieger

[57] ABSTRACT

The pouch is formed of first and second thin barrier film walls welded along the periphery to form a waste receptacle. One wall has an inlet defined by an attachment ring. The ring mounts the pouch on an adhesive faceplate adapted to adhere to the skin surrounding the stoma. A membrane, formed of material which is gas permeable but transmits little moisture and no liquid, is situated between the walls to separate the receptacle into an inlet chamber, where solids, liquid and most moisture are retained, and an outlet chamber into which gas and a small amount of vapor passes. A filter is provided to permit the gas to exit the outlet chamber. A first section of superabsorbent material isolates the filter from the outlet chamber. By absorbing any moisture in the gas before it contacts the filter, blockage of the filter is prevented. A second section of superabsorbant material is provided near the bottom of the output chamber to absorb moisture which otherwise may cause the membrane to stick to the pouch wall, resulting in a substantial reduction of the gas transmissibility of the membrane.

7 Claims, 4 Drawing Sheets

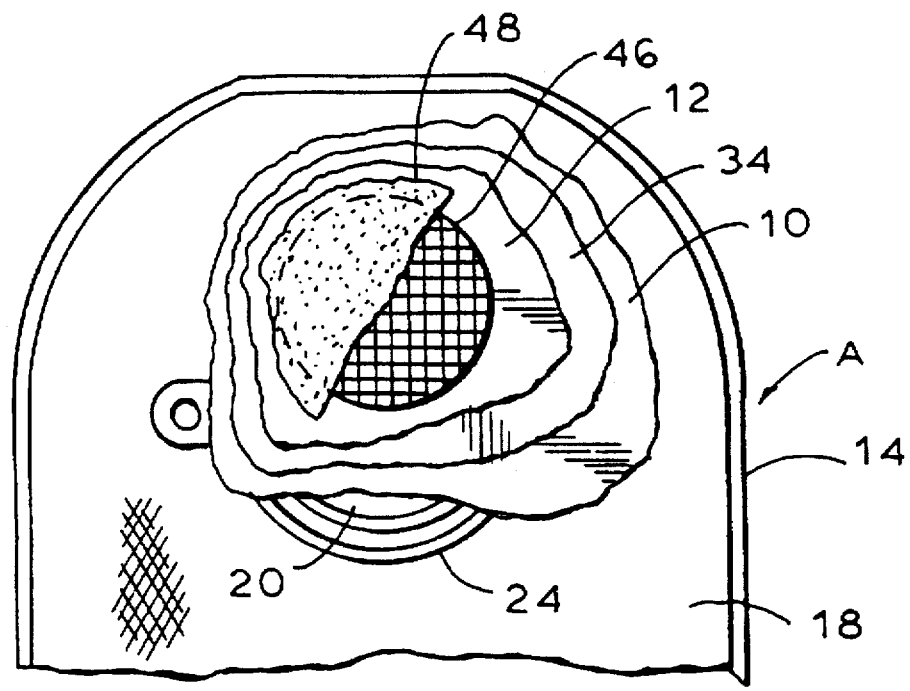
F I G. 2
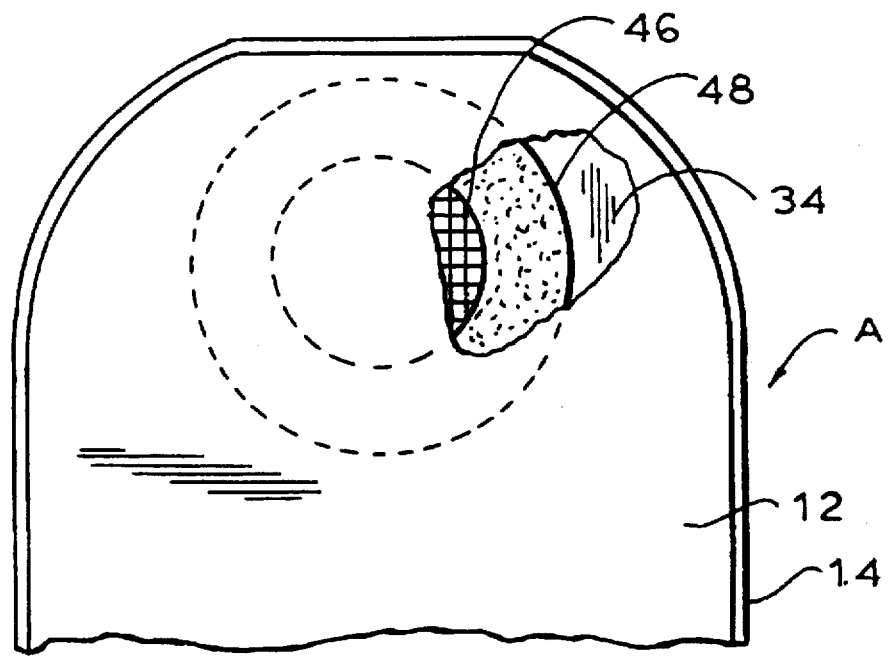
F I G. 3

OSTOMY POUCH WITH INTERVENING MEMBRANE AND SUPERABSORBENT

The present invention relates to ostomy devices and more particularly to an ostomy pouch with enhanced gas filtration properties.

Ostomy pouches of various sizes and types are designed for use by individuals who have undergone ileostomy or colostomy surgery and as a result have a stoma or artificial opening formed in the abdominal wall which serves as a discharge outlet for waste material. The ostomy pouch is affixed to the patient's abdomen over the stoma so as to collect the waste material as it is discharged. In order to prevent the escape of liquid or solid waste, it is necessary that a fluid tight seal be maintained between the pouch and the skin surrounding the stoma.

Certain problems occur as a result of the fluid tight seal. Discharge of gas from the intestine through the stoma causes the pouch to become inflated. The inflation of the pouch, which is normally visually inconspicuous, may cause embarrassment to the wearer as the pouch becomes noticeable, even through clothing. The pressure created by the gas in the pouch, if it is not allowed to escape, may build up to the point where it causes acute discomfort. In the extreme situation, a high enough pressure may cause the fluid tight seal between the pouch and the skin to be disrupted, releasing odors and possibly waste material.

In order to overcome the problems associated with the accumulation of gases within the pouch, pouches have been designed with various types of vents which control the release of the gas. In addition, such vents have been used in conjunction with replaceable deodorizing filters through which the gas must pass as it is vented.

However, the nature of the material from which the gas filter is composed is such that moisture in the form of water vapor or liquid, or solid waste material, will tend to block the filter, if permitted to contact it. Accordingly, it is known to interpose a barrier to divide the pouch into inlet and outlet chambers. The barrier may be provided with a relatively small gas opening which is offset from the inlet and vent hole. This creates a serpentine path which permits gas to pass from the inlet chamber to the outlet chamber but prevents most liquid and solid waste from entering the outlet chamber. This structure is disclosed in U.S. Pat. No. 4,411,659 issued Oct. 25, 1983 to Jensen et al.

Although the Jensen barrier is an improvement over conventional pouch structures, it does not completely eliminate moisture and liquid from entering the outlet chamber and contacting the filter. Accordingly, it has been suggested that the internal barrier be replaced by a gas-permeable, liquid impermeable membrane. One such membrane is a low density polyethylene which has been perforated and then coated by a porous polyurethane material, as disclosed in U.S. Pat. No. 5,352,316 issued Oct. 4, 1994 to Graham E. Steer.

The Steer intervening membrane is a substantial improvement over the Jensen structure. However, some problems still remained. The filter can still become blocked by a build up of moisture which is in the gas. Moreover, the gas permeability of membrane itself can became greatly diminished, preventing gas from entering the outlet chamber, if a substantial portion of the membrane becomes stuck to the interior surface of the wall of the pouch.

Our invention is designed to overcome both of these problems through the use of sections of superabsorbent material strategically situated within the pouch. In order to protect the filter from moisture in the gas, a section of suberabsorbent material is placed over the filter. It acts as a "pre-filter" to remove any moisture in the gas before the gas enters the filter. To insure the transmissibility of the entire surface of intervening membrane, a section of superabsorbent material is affixed to the interior surface of the pouch wall near the bottom of the outlet chamber. This absorbs any moisture which accumulates near the bottom of the outlet chamber and greatly reduces the possibility of the membrane sticking to the wall.

It is, therefore, a prime object of the present invention to provide an ostomy pouch where superabsorbent material is employed to prevent blockage of the vent filter by removing moisture from the gas before it passes through the filter.

It is another object of the present invention to provide an ostomy pouch of the type having an intervening membrane in which substantial reduction in the gas transmissibility of the membrane due to sticking against the surface of the pouch wall is greatly reduced by placement of superabsorbent material in the lower portion of the outlet chamber.

In accordance with one aspect of the present invention, an ostomy pouch is provided comprising first and second walls joined along at least a portion of the periphery, to define a waste receptacle. An inlet opening is situated in the first wall. Means are provided for adhering the pouch to the body with the stoma aligned with the inlet opening. A gas vent hole is present in the second wall. Filter means align with the vent hole. A section of superabsorbent material covers the filter means.

A microporous membrane is interposed between the walls so as to divide the receptical into an inlet chamber and an outlet chamber. The membrane is highly gas permeable but transmits little water vapor and substantially no liquid. A section of superabsorbent material is situated within the outlet chamber. Preferably, this superabsorbent section is situated proximate the bottom of the outlet chamber, most preferrably proximate the point on the wall where the membrane attaches to the wall.

The membrane preferrably comprises a calcium carbonate filled polyethlene microporous film.

The pouch may also include a layer of flocking mounted on the exterior surface of the first wall.

The pouch adhering means may include an adhesive faceplate. Means for mounting the faceplace to the exterior surface of the first wall is provided.

Alternately, the mounting means may include first and second coupling rings affixed to the faceplate and the first pouch wall, respectively. Preferrably, the coupling rings are detachable.

In accordance with another aspect of the present invention, an ostomy pouch is provided first and second walls joined along at least a portion of the periphery to define a waste receptical. An inlet opening in is situated the first wall. Means are provided for adhering the pouch to the body with the stoma aligned with the inlet opening. A gas vent hole is present in the second wall. A gas permeable membrane is interposed between the walls dividing the receptacle into an inlet chamber and an outlet chamber. A section of superabsorbent material is situated within the outlet chamber. Preferrably, the superabsorbent material is situated at the lower portion of the outlet chamber. Most preferrably, the superabsorbent material is affixed to the second wall proximate the point where the membrane is attached to the wall.

Filter means are provided covering the vent hole. A section of superabsorbent is mounted cover the filter means.

The membrane is highly gas permeable but transmits little water vapor and substantially no liquid. Preferably, the membrane comprises a calcium carbonate filled polyethylene microporous film.

A layer of flocking may be mounted on the exterior surface of the first wall.

The pouch adhering means may include an adhesive faceplace and means for mounting the faceplace to the exterior surface of the first wall.

Alternately, the mounting means may include first and second coupling rings affixed to the faceplace and the pouch, wall respectively. Preferrably, the coupling rings are detachable.

In accordance with another aspect of the present invention, an ostomy pouch is provided with first and second walls joined along at least a portion of the periphery to define a waste receptacle. An inlet opening is provided in the first wall. Means are provided for adhering the pouch to the body with the stoma aligned with the inlet opening. A gas vent hole is present in the second wall. A gas permeable membrane is interposed between the walls, dividing the receptical into an inlet chamber and an outlet chamber. Filter means cover the vent hole. A first section of superabsorbent material covers the filter means. A second section of superabsorbent material is situated within the outlet chamber, proximate the bottom portion thereof.

The membrane and the second wall are attached to define the bottom of the outlet chamber. The second superabsorbent section is situated proximate the point where the membrane is attached to the second wall.

To these and to such other objects which may hereafter appear, the present invention relates to an ostomy pouch with an intervening membrane and superabsorbent, as set forth in a detail in the following specification, recited in the annexed claims and illustrated in the accompanying drawings, in which like numerals refer to like parts and in which:

FIG. 2 is a partial cut away view of a portion of the pouch in FIG. 1;

FIG. 3 is a partial cut away view of the portion of the pouch seen in FIG. 2, from the reverse side;

Figure 1:
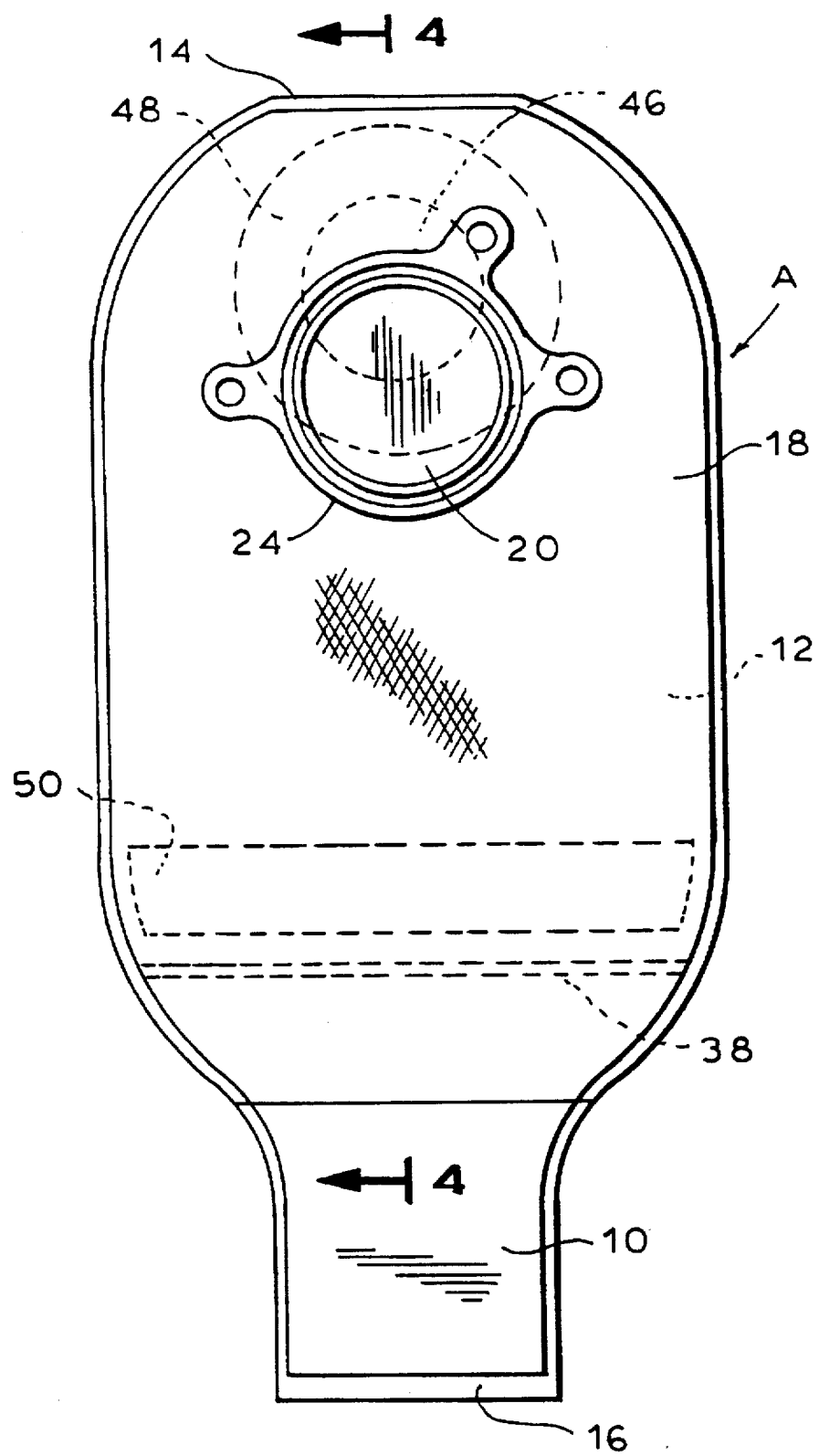
FIG. 1 is a front elevational view of the ostomy pouch of the present invention.

As seen in the drawings, the present invention is an ostomy pouch, generally designated A. Pouch A is formed of a barrier film wall 10 adapted to face the body and a rear barrier film wall 12. The walls 10, 12 are made of thin, flexible film which is heat welded around at least a portion of the periphery 14 to form an enclosed receptacle. Depending upon the type of stomal discard, the pouch may include drainable outlet 16 which is sealed with a clip (not shown) or it may include a liquid drainable tap valve (also not shown). Alternatively, the bottom merely be sealed in the same manner as periphery 14.

The films from which the pouch walls 10, 12 may be made are selected from materials which possess the properties of being moisture impermeable, odor impermeable and capable of being heat sealed or impulse welded. Suitable materials include polyethylene, copolymers of polyethylene and ethylene vinyl acetate, co-polymers of vinyl chloride and polyvinylidene chloride and laminates thereof. The pouch walls are preferably from about two to four mils thick.

In some cases, it is desirable, in order to enhance the comfort of the patient, to use a flocking material 18 for lining the exterior surface of body side wall 10. Flocking material 18 preferably has its smooth side outwards.

Figure 4:
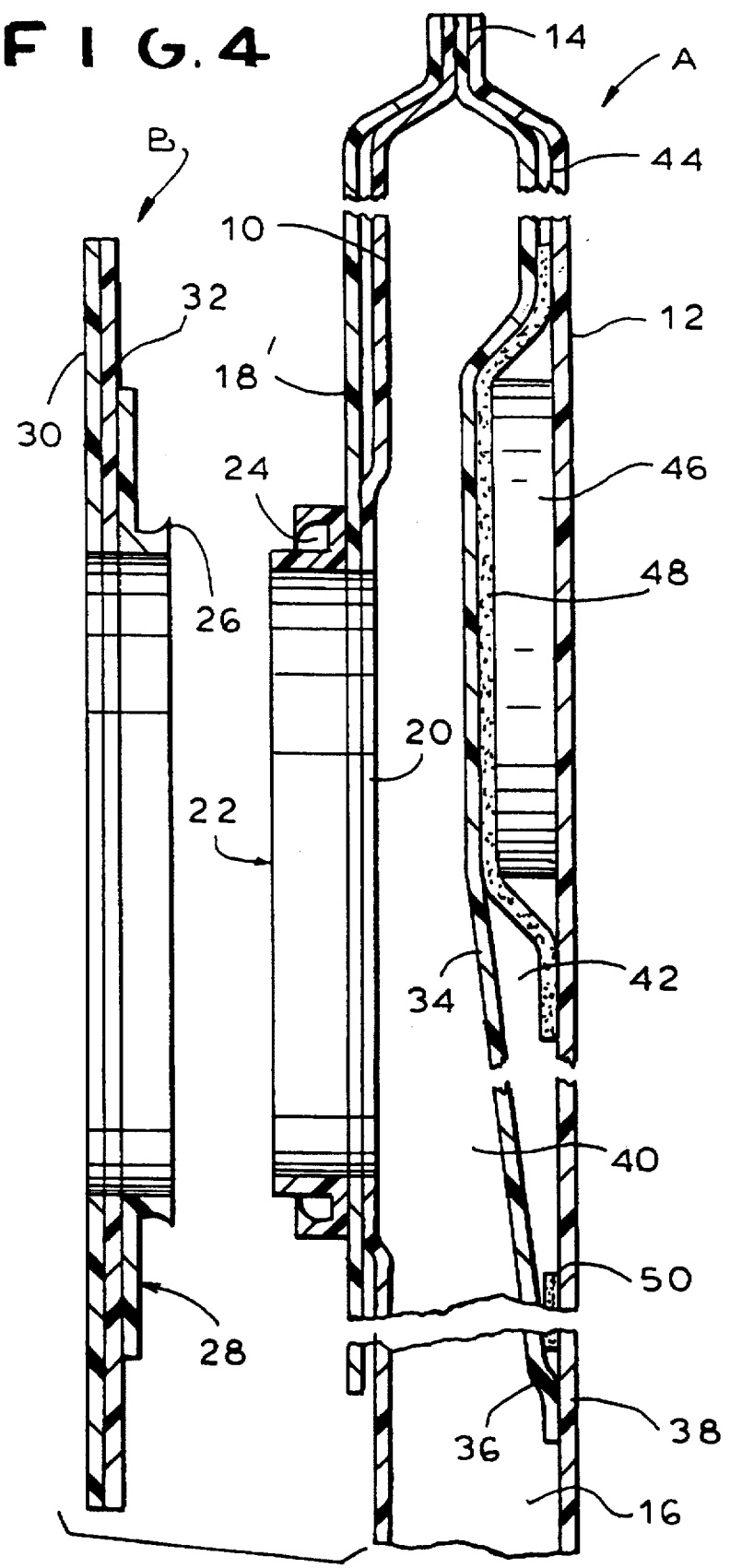
FIG. 4 is an exploded side cross-sectional view of the ostomy pouch and a mating faceplate.
Figure 5:
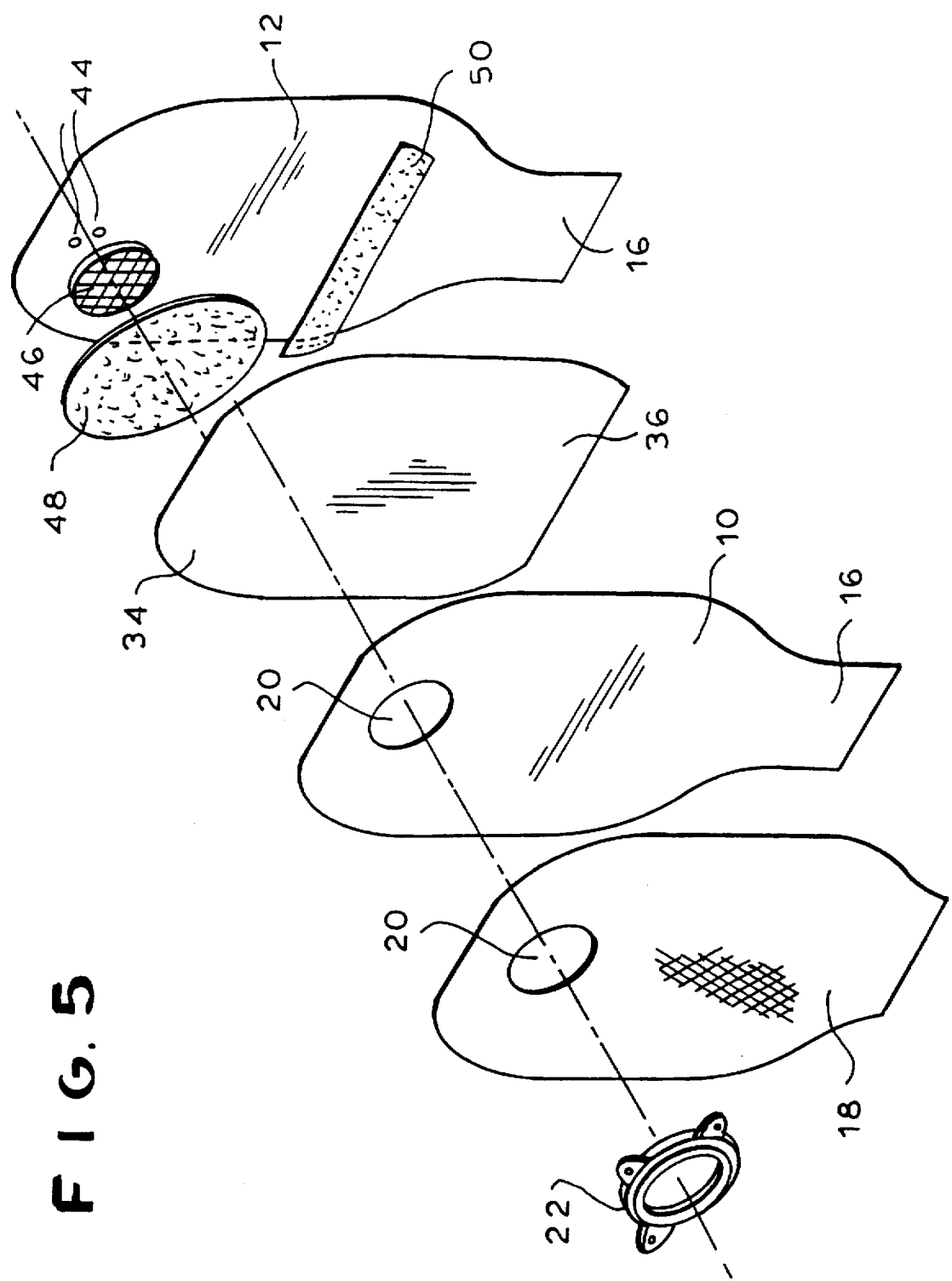
FIG. 5 is an exploded view of the ostomy pouch.

An inlet opening 20 is provided in pouch wall 10 and flocking sheet 18. A coupling ring 22 is welded directly to the exposed surface of flocking sheet 18. Ring 22 defines an annular channel 24 (see FIG. 4) into which the annular protrusion 26 of a second coupling ring 28 affixed to an adhesive faceplate, generally designated B, is removeably received to detachably mount pouch A on faceplate B.

Faceplate B is used to mount the appliance to the body and consists of a pressure sensitive adhesive layer 30 cast onto a backing 32. Layer 30 is preferrably 4 mils thick. The adhesive layer can be an acrylic microporous adhesive as taught by Copeland in U.S. Pat. No. 3,121,021, a microporous hydrocolloid adhesive as taught by Cilento in U.S. Pat. No. 4,427,727, or a polyisobutylene-hydrocolloid containing adhesive as taught by Chen in U.S. Pat. No. 3,339,546, by Chen et al. in U.S. Pat. No. 4,192,785, by Pawelchak in U.S. Pat. No. 4,393,080, or it can be adhesive composition containing a styrene type block copolymer in addition to the polyisobutylene and hydrocolloids as taught by Doyle et al. in U.S. Pat. No. 4,551,490.

The backing 32 of the faceplate may include a non-woven polyethlyene material. Coupling ring 28 is welded to the non-adhesive surface of backing 32.

As is common with removeable ostomy pouches, coupling rings 22 and 28 interengage to form a fluid tight seal such that the device firmly adheres to the skin surrounding the stoma with the stoma aligned with inlet opening 20. When the pouch requires cleaning or replacement, ring 22 is detached from ring 28 and the pouch is removed. Alternatively, the invention can be provided in a one piece version, where the adhesive faceplate is welded permanently to the pouch.

Interposed between walls 10 and 12 of pouch A is a microporous intervening membrane 34. The periphery of membrane 34 is sealed between the edges of walls 10 and 12 along periphery 14, except along the bottom edge 36. Bottom edge 36 of membrane 34 is welded along line 38 to the interior surface of wall 12 such that the interior of the pouch is divided into two chambers, an inlet chamber 40 and an outlet chamber 42. The weld for the membrane may be accomplished at the time the walls are welded together. Welding the membrane to the pouch wall in this fashion permits washing of the inlet chamber of the pouch.

Membrane 34 is a breathable microporous film which is a barrier to most moisture and to liquid and solids, while freely transmitting gas. It can be composed of polyethylene filled with calcium carbonate or chalk. One such commercially available material which can be used for this purpose is sold under the trademark EXXAIRE XBF-100W by the Exxon Chemical Company.

Under normal conditions, membrane 34 should permit all gas and a small amount of moisture in the form of vapor to pass from inlet chamber 40 to outlet chamber 42. Most moisture, and all liquid and solids should remain in the inlet chamber.

A vent hole 44 is present in wall 12. A carbon filter 46 of conventional design is welded to the interior surface of wall 12 over hole 44, such that gas in outlet chamber 42 will pass through filter 46 before exiting from vent hole 44. However, the gas which passes through the membrane carries with it some moisture. This moisture may accumulate in the filter and will evently block the filter.

In order to prevent the moisture from contacting the filter, a circular section 48 of superabsorbent material is affixed to the interior surface of wall 12 to cover filter 46 and isolate it from the outlet chamber. Section 48 absorbs any moisture in the gas which may have passed through membrane 34 into the outlet chamber, before the gas passes through the filter. Section 48 may be formed of an acrylic water-absorbing resin carried on a nonwoven substrate. One such material is commercially available from Gelok, Inc. of Dunbridge, Ohio under the designation Gelok 6600 A/A.

A elongated section 50 of the same superabsorbent material is affixed to the interior surface of wall 12 near the bottom of outlet chamber 42 proximate the point 38 where lower edge 36 of membrane 34 is attached to wall 12. Section 50 functions to absorb any additional moisture or liquid which may be present in outlet chamber 42. Elimination of this moisture prevents membrane 36 from sticking to the interior surface of wall 12 and thereby blocking the surface of the membrane. Blockage of a substantial amount of the surface area of the membrane will greatly reduce the transmission of gas through the membrane and into the outlet chamber.

It should now be appreciated that the present invention utilizes superaborbent material sections in the outlet chamber to isolate the vent filter to prevent blockage thereof and to remove moisture which may cause sticking of the microporous membrane to the pouch wall, reducing the gas permeability of the membrane. The result is an ostomy filter with improved gas flow properties and a longer useful life.

While only a single preferred embodiment of the present invention is disclosed herein for purposes of illustration, it is obvious that many variations and modifications could be made thereto. It is intended to cover all of these variations and modifications which fall within the scope of the invention, as defined by the following claims.

We claim:

1. An ostomy pouch for collecting waste from a stoma on a human body comprising first and second walls joined along at least a portion of their peripheries to define a waste receptacle, an inlet opening in said first wall, means for adhering the pouch to the body with the stoma aligned with said inlet opening, a gas vent hole in said second wall, a gas permeable and liquid-impermeable membrane interposed between said walls, dividing said receptacle into an inlet chamber and an outlet chamber, a filter member covering said vent hole, a first section of superabsorbent material covering said filter member for removing moisture and thereby retarding blockage of said filter and a second section of superabsorbent material situated within said outlet chamber and apart from said filter member for removing moisture from said outlet chamber and thereby retarding blockage of said membrane by said second wall.

2. The pouch of claim 1 wherein said second superabsorbent section is situated proximate the bottom of said outlet chamber.

3. The pouch of claim 1 wherein said membrane comprises a calcium carbonate filled polyethylene microporous film.

4. The pouch of claim 1 further comprising a layer of flocking mounted on the exterior surface of said first wall.

5. The pouch of claim 1 wherein said pouch adhering means comprises an adhesive faceplate and means for mounting said faceplate to the exterior surface of said first wall.

6. The pouch of claim 5 wherein said mounting means comprises first and second coupling rings affixed to said faceplate and said pouch, respectively.

7. The pouch of claim 6 wherein said coupling rings are detachable.

* * * * *